US009310280B2

(12) United States Patent
Reynolds et al.

(10) Patent No.: US 9,310,280 B2
(45) Date of Patent: Apr. 12, 2016

(54) BALLAST WATER TREATMENT MONITORING SYSTEM

(71) Applicant: The Glosten Associates, Inc., Seattle, WA (US)

(72) Inventors: Kevin J. Reynolds, Seattle, WA (US); James Wolfe, Seattle, WA (US); Jake Parks, Bremerton, WA (US)

(73) Assignee: The Glosten Associates, Inc., Seattle, WA (US)

( * ) Notice: Subject to any disclaimer, the term of this patent is extended or adjusted under 35 U.S.C. 154(b) by 210 days.

(21) Appl. No.: 13/794,153

(22) Filed: Mar. 11, 2013

(65) Prior Publication Data

US 2014/0000384 A1    Jan. 2, 2014

Related U.S. Application Data

(60) Provisional application No. 61/646,682, filed on May 14, 2012.

(51) Int. Cl.
*G01N 1/20* (2006.01)
*G01F 1/46* (2006.01)
*B63J 4/00* (2006.01)
*G01N 1/22* (2006.01)

(52) U.S. Cl.
CPC . *G01N 1/20* (2013.01); *B63J 4/002* (2013.01); *G01F 1/46* (2013.01); *G01N 1/2035* (2013.01); *G01N 2001/225* (2013.01)

(58) Field of Classification Search
CPC .......... G01F 1/46; G01N 1/20; G01N 1/2035; G01N 2001/225; B63J 4/002

USPC ................ 73/863.03, 863.51, 863.58, 863.83
See application file for complete search history.

(56) References Cited

U.S. PATENT DOCUMENTS 2,327,111 A * 8/1943 Kimmell .................... 73/863.12
3,765,226 A * 10/1973 Strickland et al. ......... 73/863.58
(Continued)

FOREIGN PATENT DOCUMENTS

| DE | 112008002979 B4 | | 9/2013 |
| JP | 2009-115500 | * | 5/2009 |
| KR | 10-2010-0103487 A | | 9/2010 |

OTHER PUBLICATIONS

Richard, R.V., et al., "Analysis of Ballast Water Sampling Port Designs Using Computational Fluid Dynamics," Final Report No. CG-D-01-08, U.S. Coast Guard Research and Development Center, Groton, Conn., Feb. 2008, 62 pages.

(Continued)

*Primary Examiner* — Daniel S Larkin
(74) *Attorney, Agent, or Firm* — Christensen O'Connor Johnson Kindness PLLC

(57) ABSTRACT

A method and system for taking a sample of ballast water. The method includes withdrawing a sample of ballast water via a tube inserted in a ballast water pipe, wherein the tube includes a sample inlet, and isokinetic flow is achieved via a pump that controls the flow of the sample ballast water through the tube inlet by comparing a flow of the ballast water pipe with a flow of the sample ballast water through the tube; and controlling the flow of water through the sample tube inlet when a flow of the ballast water pipe is sensed to be different; withdrawing a portion of the sample ballast water for testing; and returning remaining sample ballast water to the ballast water pipe.

6 Claims, 8 Drawing Sheets

(56) References Cited

U.S. PATENT DOCUMENTS

| | | | | |
|---|---|---|---|---|
| 4,018,089 | A | * | 4/1977 | Dzula et al. ............. 73/863.58 |
| 4,413,533 | A | * | 11/1983 | Diesel .................... 73/863.31 |
| 5,763,794 | A | | 6/1998 | Marrelli |
| 7,717,000 | B2 | * | 5/2010 | Xie .................... B01F 5/0682 73/863.03 |
| 2009/0223309 | A1 | | 9/2009 | Kurz |
| 2010/0145634 | A1 | | 6/2010 | Pinguet et al. |

OTHER PUBLICATIONS

International Search Report and Written Opinion mailed Jun. 14, 2013, issued in corresponding International Application No. PCT/US2013/030237, filed Mar. 11, 2013, 8 pages.

* cited by examiner

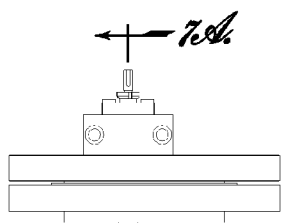
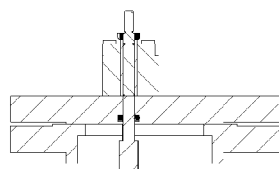
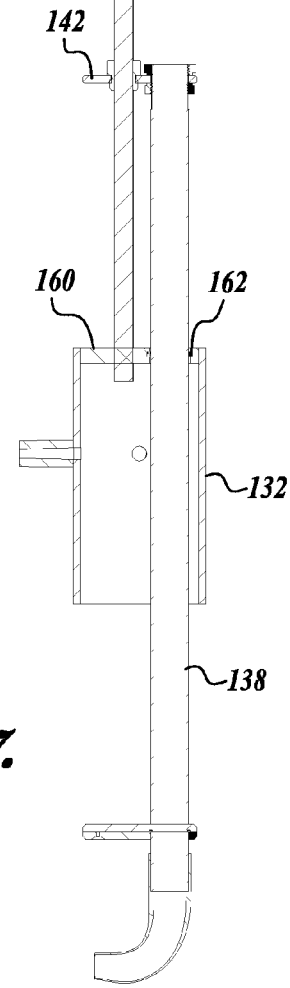
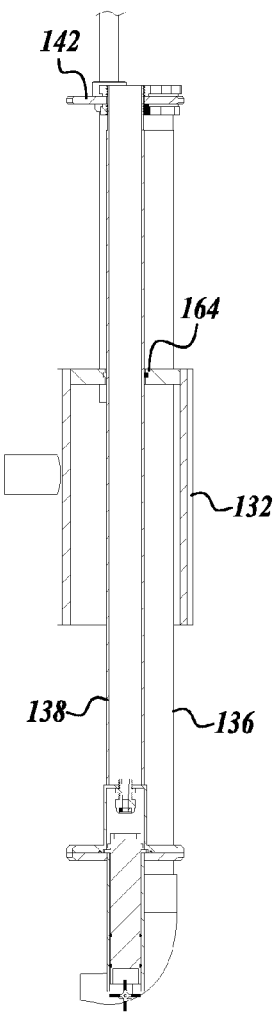
Fig. 7.    Fig. 7A.    Fig. 7B.

BALLAST WATER TREATMENT MONITORING SYSTEM

CROSS-REFERENCE TO RELATED APPLICATION

This application claims the benefit of U.S. Provisional Application No. 61/646,682, filed on May 14, 2012, incorporated herein by reference in its entirety.

BACKGROUND

Many regulations exist for the treatment and discharge of ballast water by marine vessels. Ship ballast water treatment systems are typically tested by an independent laboratory. These laboratories, even when following mandated test protocols, are not able to replicate all of the variability in organism populations, water chemistry, and environmental conditions that a marine vessel will encounter during operations. This leads to uncertainty that ballast water treatment systems will be effective in varied conditions. Marine vessel operators and regulatory agencies need tools and methods for reliable sampling of ballast water to allow these determinations to be made.

SUMMARY

One of the primary concerns when sampling ballast water to determine compliance with standards is the ability to obtain a representative sample. A sample is representative if it is gathered in a way to minimize any bias from the bulk fluid and is large enough to provide statistical significance from the results.

Minimizing bias in the sample is primarily a function of the sampling method and geometry of sampling equipment. Using a clean system (free of potential contaminants) with a pitot-type sampler at isokinetic flow conditions minimizes sampling bias at the sample location. The sample location within the ballast system also will affect bias. Sampling from a long, straight section of pipe where the flow is fully developed with minimal turbulence is the best case for a sample point.

In one embodiment, an isokinetic flow velocity is achieved by the use of a pump downstream of a pitot tube assembly. A first flow sensor on the pitot tube assembly senses the ballast water flow velocity in the ship's ballast water pipe near the sampling point. A second flow sensor measures the flow rate of the sampled fluid at the pitot tube. The control system may receive these two signals and instruct the pump controller to change speeds in order to maintain an isokinetic sampling condition. In one embodiment, in combination with the sampling flow control, the pitot tube can be made equal to the isokinetic diameter.

The sensors and controls associated with the system may determine the water flow velocity in the ballast pipe and adjust the sampling pump speed to maintain isokinetic flow conditions at the sample point. This allows the pitot sampler assembly to be used in nearly any marine vessel with equal effectiveness. The sampling system increases and decreases sampling rates as the main ballast water system changes flow rates, allowing the sampling system to maintain isokinetic conditions as flows change during operations.

The pitot tube assembly allows flow-through sampling and analysis processes using a single connection to the ballast system. This is an improvement over current systems, which require either dumping sampled water into the marine vessel bilges or into a secondary connection where resulting samples can be pumped.

The pitot tube assembly connects to and inserts through a shipboard isolation valve. This allows the system to be connected to a ballast system without interrupting operations. This is an improvement over current practice that requires ballasting to stop and possible drainage of that ballast water piping both prior and after the sampling occurs.

The closed-loop design with a single connection to the ballast system means that there is very low differential pressure across the sampling system. This allows the use of a small circulation pump. This closed-loop design also provides a consistent pressure differential, allowing the selection of a single pump for all applications.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 7 is a diagrammatical illustration of a portion of the pitot tube assembly;

FIG. 7A is a diagrammatical cross sectional illustration of a portion of the pitot tube assembly;

FIG. 7B is a diagrammatical cross sectional illustration of a portion of the pitot tube assembly.

DETAILED DESCRIPTION

Figure 1:
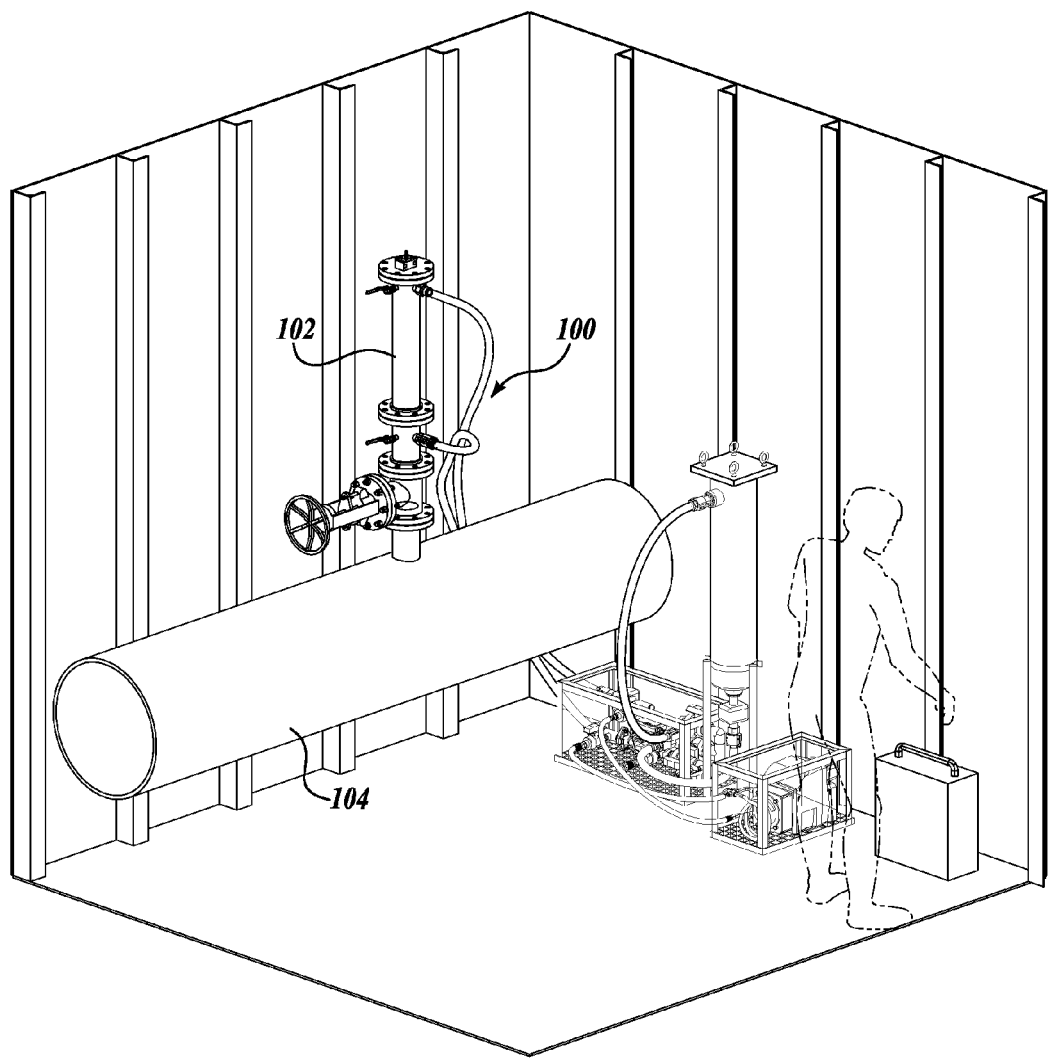
FIG. 1 is a diagrammatical illustration of a ballast water sampling system.

Referring to FIG. 1, a sampling system 100 is illustrated. The system 100 may be used to withdraw samples of fluids and, in particular, ballast water from a ship's ballast water system. However, the description of the sampling system used in sampling ballast water is merely to describe representative embodiments and should not be construed as limited for use in only sampling ballast water. The system is able to filter organisms larger than 50 µm in minimum dimension from the ballast water and allow removal of the organisms for off-site processing. Additionally, the system is capable of removing a small sample of raw ballast water from the ship's ballast water pipe for off-site processing.

The water sampling system is connected to the ship's ballast water pipe 104 via the pitot tube assembly 102. The pitot tube assembly 102 includes a housing 108 and a pitot wand 110 within the housing. The pitot wand 110 can be extendable and retractable within the housing 108 to reach the interior of the pipe 104.

The ballast water for sampling may be drawn from a ship's ballast water pipe 104 using the pitot tube assembly 102 that can be inserted into the pipe 104 during periods of ballast water flow through the pipe 104. The sample water is passed through a filter and returned to the ballast water pipe 104 by a circulation pump.

Figure 2:
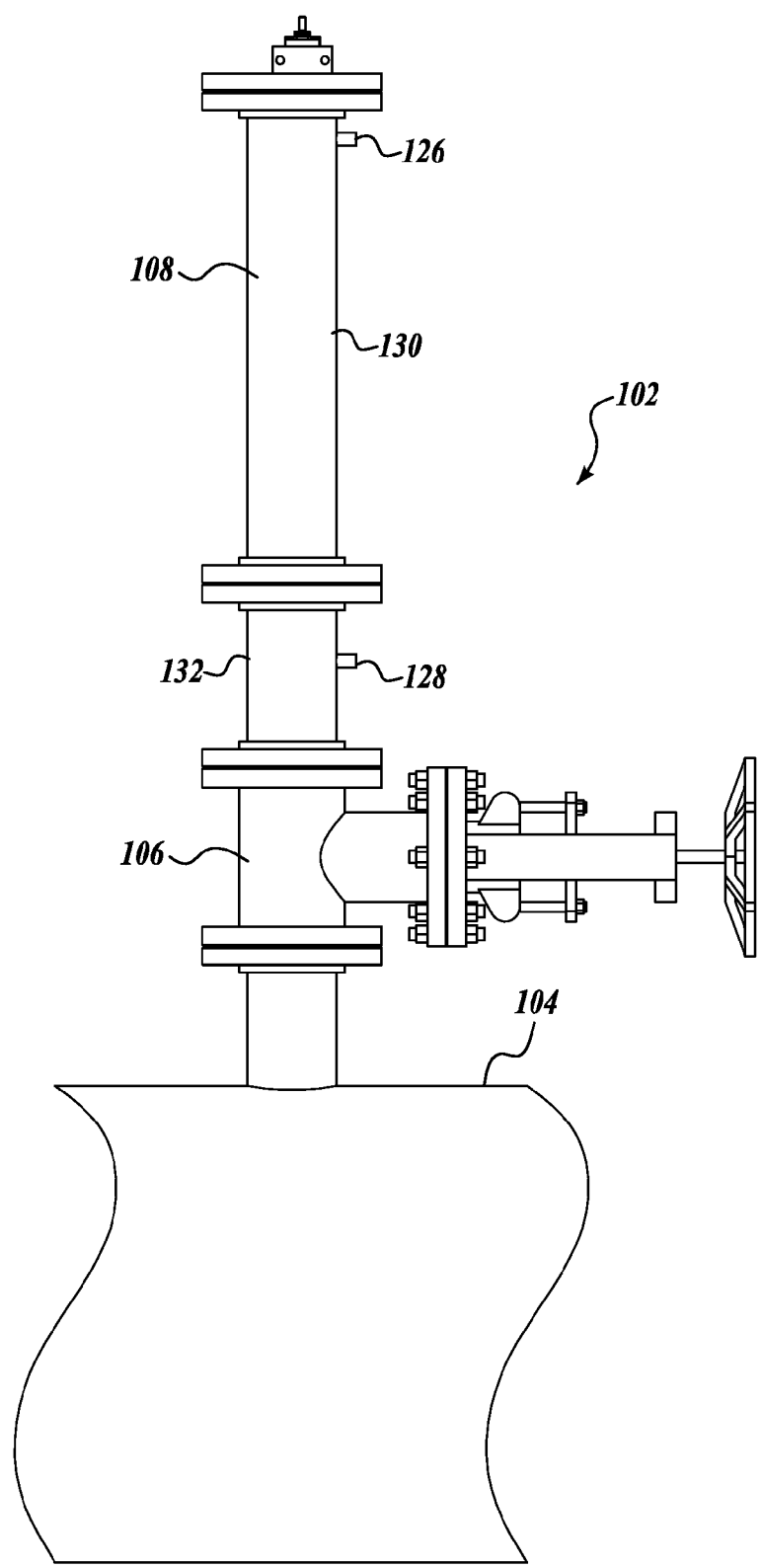
FIG. 2 is a diagrammatical illustration of a pitot tube assembly.
Figure 3:
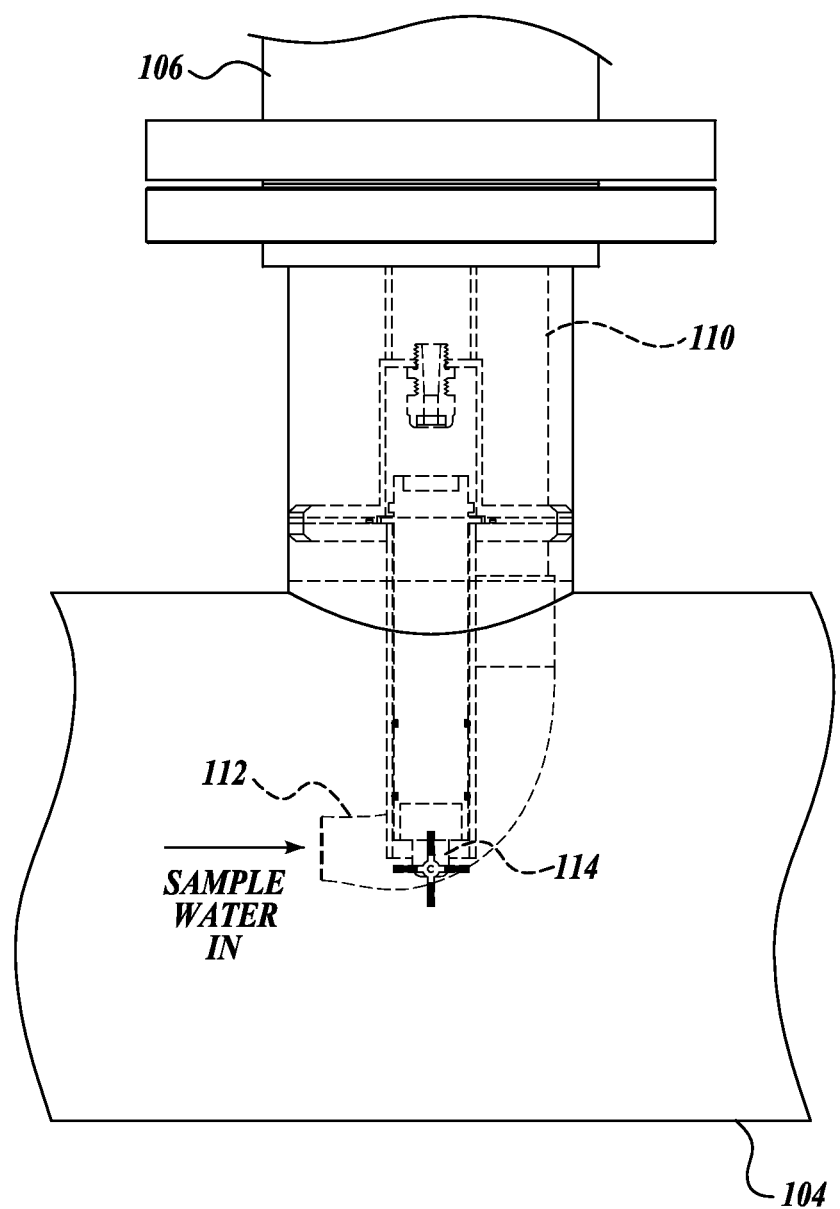
FIG. 3 is a diagrammatical illustration of the pitot tube assembly.

As illustrated in FIGS. 2 and 3, the pitot tube assembly 102 can be mounted on an isolation valve 106 extending from and connected to any ship's ballast water-carrying pipe 104. The pitot tube assembly 102 can be mounted in any orientation, vertical being merely representative. The valve 106 can be a fully ported valve so as to allow the pitot wand 110 to be lowered therethrough to reach into the pipe 104, as illustrated in FIG. 3 to be able to withdraw a sample from pipe 104. The housing 108 can include a longer upper section 130 and a relatively shorter lower section 132. The sections can be joined by the use of flanges, known in the art. The pitot tube assembly 102 also includes an upper flange to close the upper end thereof and a lower flange with an open center is attached at the bottom. The lower flange can be bolted to the ship's isolation valve 106.

As described further below, the pitot tube assembly 102 can obtain a ballast water sample under isokinetic flow conditions. As used herein, isokinetic flow is established under conditions where the velocity of the sample ballast water being obtained at the pitot tube is the same or substantially the same as the velocity of the ballast water flowing in the pipe 104 at the sample point (bulk velocity). The pitot tube assembly 102 is designed to achieve isokinetic sampling flows from approximately 0 to 3.5 meters per second (0 to 12 feet per second), for example. However, other flow velocities are possible.

Referring to FIG. 3, sample water is drawn from the pipe 104 through a pitot tube 112 and then up through the wand 110 and out the nozzle 126 (best seen in FIG. 2) on the upper end of the housing 108. Once the sample water has been processed, for example, being filtered and a sample being removed for testing, the ballast water is returned through the return water nozzle 128 (best seen in FIG. 2) on the housing 108. Two small nozzles can be provided at the upper and lower ends of the housing 102 to allow the system to be vented and drained during setup and removal.

Figure 4:
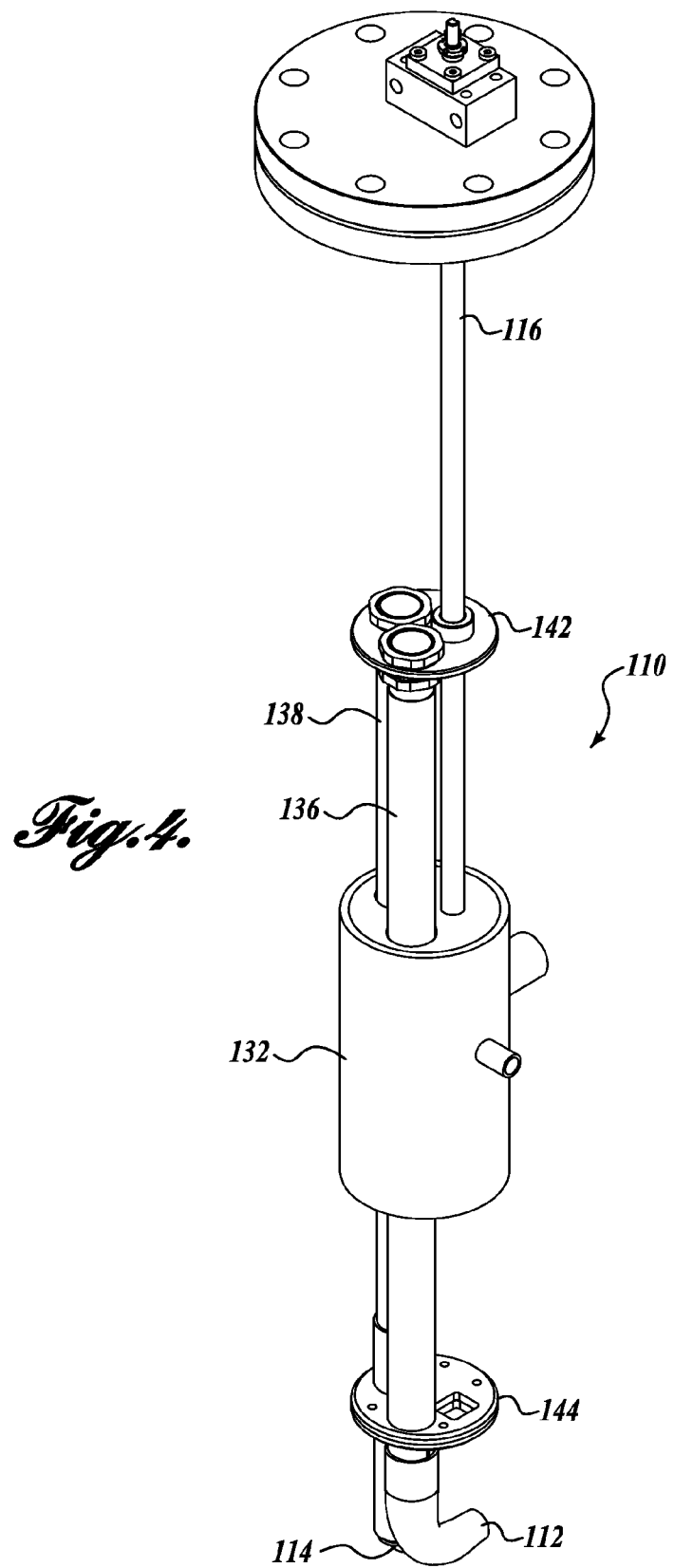
FIG. 4 is a diagrammatical illustration of a portion of the pitot tube assembly.

As illustrated in FIG. 4, the pitot tube assembly 102 of FIG. 2 includes an internal pitot wand 110. The bottom end of the pitot wand 110 is provided with a pitot tube 112, which ends in a 90 degree elbow and serves as the water sample inlet. The bottom of the pitot wand 110 also includes a flow-sensing instrument 114, such as a paddle wheel sensor, for sensing the velocity of ballast water in the pipe 104. The pitot tube 112 and flow-sensing instrument 114 are mounted on two elongated members 136, 138, respectively. Conventionally, a pitot tube is used to measure the pressure of a stagnant fluid. However, as used herein, "pitot tube" denotes the inlet nozzle 112 for withdrawing sample water that is not stagnant.

The pitot wand 110 is lowered into the ballast water pipe 104 through the opened fully ported isolation valve 106 using, for example, a jackscrew 116 (or Acme screw). Jackscrews are known to be used in changing rotary motion into linear up and down motion, such as would be used to raise and lower the pitot wand 110. However, it is to be appreciated that the pitot tube assembly 102 can be mounted in any configuration depending on the location of the isolation valve 106.

Figure 5:
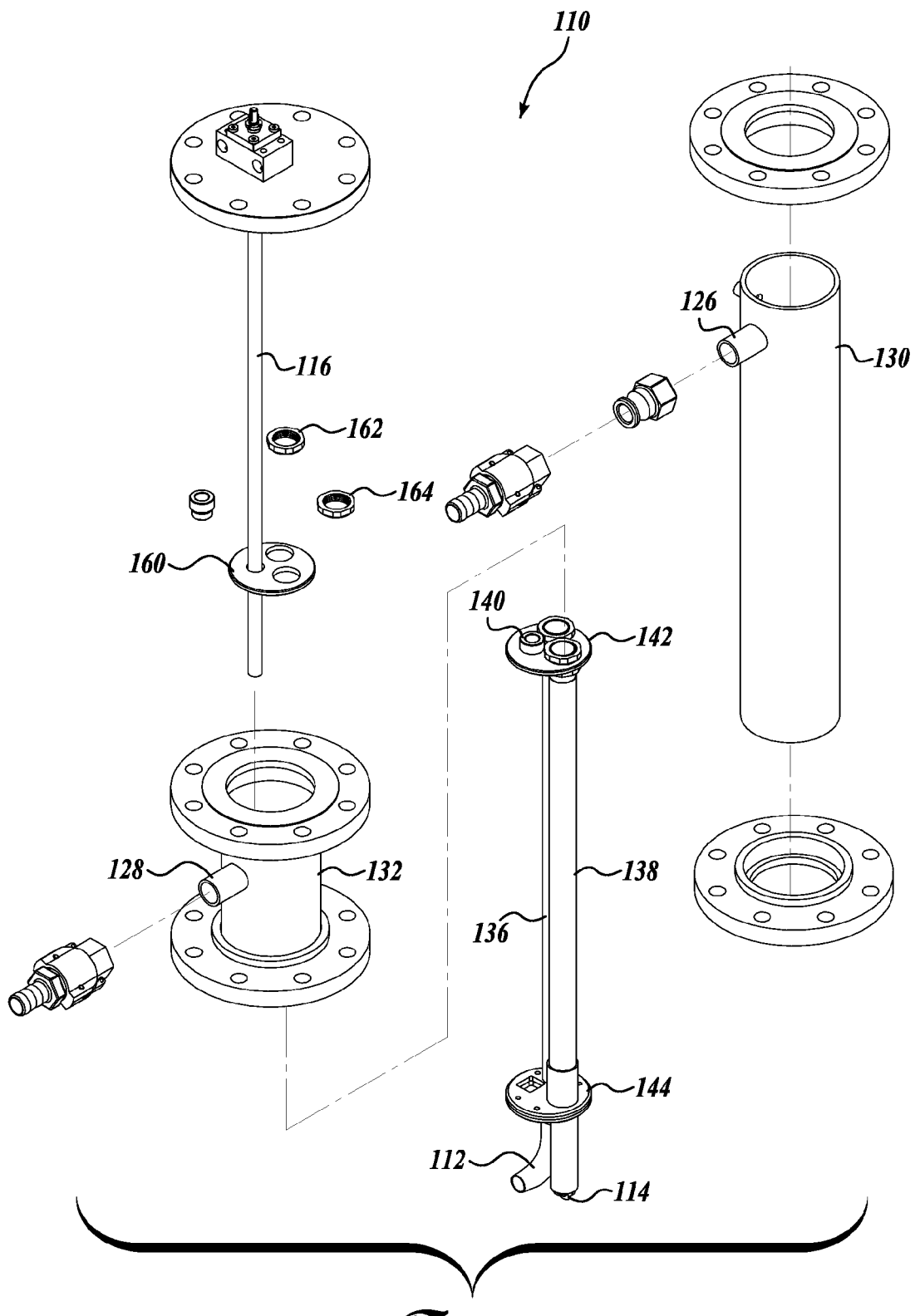
FIG. 5 is an exploded diagrammatical illustration of a pitot tube assembly.
Figure 6:
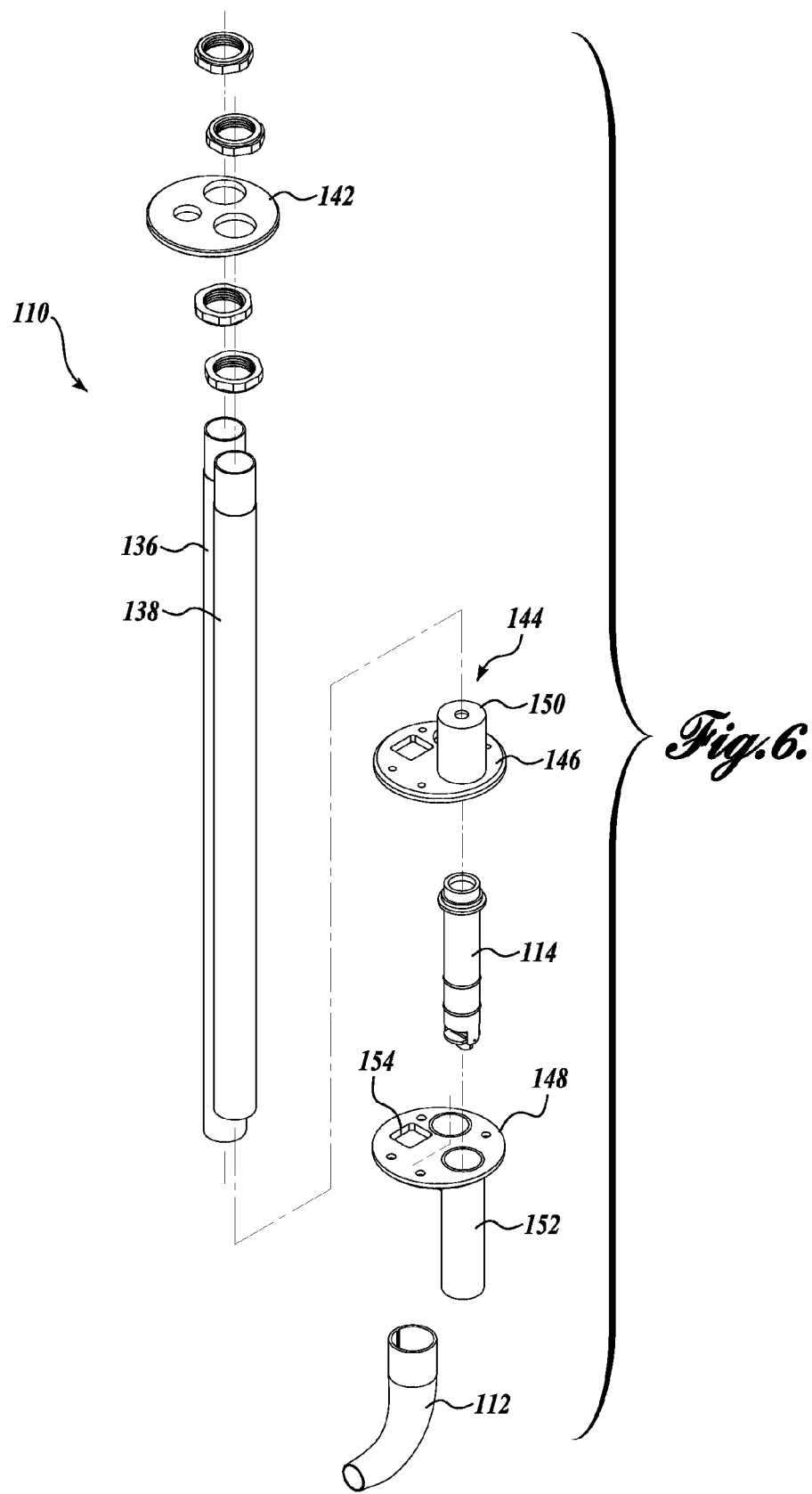
FIG. 6 is an exploded diagrammatical illustration of the pitot wand.

Referring to FIGS. 5 and 6, the pitot wand assembly 110 is more fully illustrated.

The pitot wand 110 is constructed from a first 136 and second 138 elongated hollow member. The pitot tube 112 is connected to the lower end of the hollow member 136, and is for withdrawing sample ballast water. The hollow member 136 terminates at and is rigidly connected to a connecting plate 142. The outer periphery of the connecting plate 142 is sized to allow vertical movement within the inside diameter of the upper section 130 of the housing.

The flow-sensing instrument 114 is connected to the lower end of the member 138. The member 138 also terminates at, and is rigidly connected to, the connecting plate 142. The member 138 can be for routing electrical conduit, such as for powering and receiving signals from the flow sensor 114 connected at the bottom end of the member 138.

The pitot wand 110 includes a lower flange 144 that can be rigidly attached at the lower sections of members 136 and 138. Referring to FIG. 6, the lower flange 144 construction is more clearly seen. The flange 144 includes an upper section 146 and lower section 148. The upper section 146 includes an upward projecting holder 150 for receiving the flow measuring instrument 114. The upper section 146 is then inserted via the projecting holder 150 in the lower end of the hollow member 138. The lower section 148 of the flange 144 includes a downward projecting hollow tube 152 to house the flow measuring instrument 114, such that a paddlewheel-type flow sensor, for example, can project below the end of the hollow tube 152. The lower section 148 can be assembled rigidly to the upper section 146. The lower flange 144 has an outer diameter that is sized to fit within the inner diameter of the housing 108 so as to align the pitot wand 110 as it is raised and lowered within the housing 108.

Referring to FIG. 5, the elongated members 136, 138 are held together by the upper connecting plate 142 and the lower flange 144 to move in the housings 130, 132, as a unit. The connecting plate 142 also includes a nut 140 that receives the Acme screw 116. As can be appreciated, turning the Acme screw 116 will raise and lower the two members 136 and 138 simultaneously within the housings 130, 132.

The newly collected sample water and return sample water are separated. The water sample is drawn through the pitot tube 112 and exits from the top of the member 136. The water sample then exits from the housing 130 through the water outlet 126. After processing the water sample, the water sample is returned via the water return inlet 128 in the lower housing 132. The newly drawn water sample is separated from the return water sample via the use of a plate 160 positioned at the top of the lower housing 132. The plate 160 includes seals 162 and 164 (best seen in FIGS. 7A, 7B) that surround the members 136, 138, respectively, to prevent the contamination of the newly drawn water sample with the return water sample. The seals 162, 164 also allow the members 136, 138 to slide therein when being raised and lowered.

Because the upper end of the hollow member 136 is hollow, it can be appreciated that the water sample taken up by the pitot tube 112 will exit the member 136 above the seal plate 160 and then enter the upper section 130 of the housing and be withdrawn through the water outlet nozzle 126. The return water sample will enter via the inlet nozzle 128 in the lower section 132 of the housing below the seal plate 160, pass through the lower flange 144 via a hole 154, and exit into the ship's pipe 104.

The pitot wand 110 includes an inlet nozzle 112 (the pitot tube), which is set generally at a right angle to the longitudinal axis of the pitot wand 110 and is pointed with the open end in the direction of flow of the ballast water through the ballast water pipe 104. It is to be appreciated that the pitot wand 110 is generally inserted in a direction that is perpendicular to the ballast water pipe 104. In the illustrated case, the pitot wand 110 is set vertically because the illustrated ballast water pipe 104 is set horizontally. Therefore, in the illustrated embodiment, the inlet nozzle 112 is set horizontally and aligned with the ballast water pipe 104. It is to be appreciated that if the ballast water pipe 104 is set vertically, then the pitot tube assembly 102 may result in being horizontal. The ballast water sample inlet 112 is generally parallel to the direction of flow of the ballast main pipe 104. The opening in the inlet nozzle 112 leads to the passage 136 within the interior of the pitot wand 110.

Referring to FIG. 5, the pitot wand 110 is positioned in the housing sections 130, 132 such that the connecting plate 142 and the open upper end of the member 136 are above the seal plate 160. When withdrawing sample ballast water, the pitot wand 110 is lowered and the shaft seals 162, 264 remain in place on the seal plate 160 at the upper end of the housing 132, such that the open end of the member 136 remains above the seal plate 160 and the sample water return inlet 128. The lower flange 144 remains below the seal plate 160 and the sample water return inlet 128. The ballast water sample is returned to the ballast water pipe 104 via the sample water return inlet 128 on the lower section 132 of the housing. The return sample water exits the housing 108 around the pitot wand 110 at the lower end thereof, which then leads into the ballast water pipe 104. The return sample water is released behind the pitot tube 112, and behind the flow measuring instrument 114.

In one embodiment, the pitot wand and assembly can minimize bias of entrained solids (such as organisms) in the sample fluid relative to the bulk fluid.

In one embodiment, the pitot tube assembly 102 can withdraw a 3 cubic meter sample in 90 minutes, with a ballast water fluid velocity of approximately 1.8 meters per second. This requires an open area at the pitot tube 112 mouth of approximately 0.5 square inches for isokinetic flow.

In one embodiment, smooth flow around the pitot tube 112 is ensured, and the mouth of the pitot tube 112 is smooth in profile, including round and oval shapes at the proximal (front) side of the wand 110, and a rounded shape at the distal (back) side.

In one embodiment, the mouth of the pitot tube 112 is greater than 1 diameter upstream of any downstream interference in the ballast water pipe 104.

In one embodiment, the maximum velocity to maintain isokinetic flow is approximately 3.6 meters per second.

In one embodiment, the flow speed of the sampled fluid downstream of the pitot tube can change from the isokinetic velocity, but can remain smooth with minimal turbulence-causing geometry.

In one embodiment, a flow sensor 114 is used to measure the speed of the flow in the ballast main pipe 104 to ensure that the flow velocity at the pitot tube 112 is near or approximately isokinetic. The flow sensor should be in the free stream and can be removable for maintenance. In one embodiment, the flow sensor 114 uses a paddle wheel-type flow sensor on the bottom of the pitot wand 110. However, other flow sensor types may be used. For example, in one embodiment, ultrasonic sensors can be used on the exterior of the ballast water pipe 104.

As used herein, isokinetic sampling occurs when the velocity of the fluid and the bulk flow in the ballast water pipe 104 matches the velocity of the fluid at the inlet of the sample tube 112. Isokinetic sampling is useful when sampling a fluid that contains entrained solids or fluids with a density different than the carrier fluid in order to obtain a representative sample. In the disclosed system and method, the diameter of the pitot tube 112 is made a fixed size and can be used in many different flow speeds because of the ability to reach isokinetic flow velocity via the use of sensing ballast water flow velocity in pipe 104 and sample flow velocity, and then calculating a difference in flow velocities and operating a sample water pump so that the sample water flow velocity in the pitot 112 matches the ballast water flow velocity in pipe 104.

The isokinetic diameter for a sampling pitot tube can be calculated based on the fluid flow rate through the main ballast pipe, the fluid flow rate through the sampling apparatus, and the diameter of the ballast main pipe. The isokinetic diameter is a well-known number for sizing sample ports as disclosed in *Computational Fluid Dynamics Analysis of Ballast Water Sampling*, by E. Lemieux et al.

A feature of the pitot tube assembly disclosed herein is the ability to be universally used in various ballast water systems regardless of flow of the ballast water, meaning that the system can be installed with equal effectiveness on vessels of different sizes. Different vessels have different ballast water flow rates, volumes, pipe sizes, etc. In order to use the same equipment with equal effectiveness on any vessel, a sampling pump is used to modify the flow velocity enough through the pitot wand to achieve desirable sampling conditions. Thus, the sample pitot tube 112 diameter is not increased larger than the isokinetic diameter, which is the current common method.

In one embodiment, the use of the pitot tube assembly 102 is as follows.

Assuming that the ship ballast water system includes an isolation valve as described, the valve is initially closed, and vessel personnel unbolt the blank flange covering the sample port in the ballast water pipe 104. Then, the pitot tube assembly 102 is bolted onto the shipboard flange upstream from the closed valve. Hoses may be connected from the sampling system to the pitot tube assembly 102. The isolating valve 106 is opened. The pitot wand 110 is lowered into the ballast water pipe 104 by operation of the jackscrew system 116.

The valves in the sampling rig are aligned, and sampling can begin. Once the sampling testing is complete, the pitot wand 110 is retracted by the jackscrew 116, and the isolating valve 106 is closed. Thereafter, the pitot tube assembly can be drained and removed from the valve 106 and the blank flange reinstalled on top of the valve 106.

In one embodiment, the sampling system may include a controller (PLC 226 of FIG. 8) and data recorder with an HMI interface. The purpose is to provide one controller that can manage and record data from all other subsystems. The controls and equipment may be contained in a rugged, portable case with interface ports that may allow for connecting to the sub-assemblies for pump control, data acquisition, etc.

In one embodiment, a programmable logic controller (PLC 226) may be used to collect the input from all sensors and control the sampling pumps.

The PLC 226 may control the operation and speed of the pump motors, as well as provide the link to the HMI for data display and data logging. The PLC 226 may be a modular type to allow any necessary customization and to allow for implementation of future technologies.

In one embodiment, the majority of interface to the control system may occur through a touch screen interface. Touch screen interfaces are commercially available displays that may have integrated data logging capabilities. Integrating HMI and data logging is useful, since the amount of programming to interface to the PLC is reduced considerably.

Figure 8:
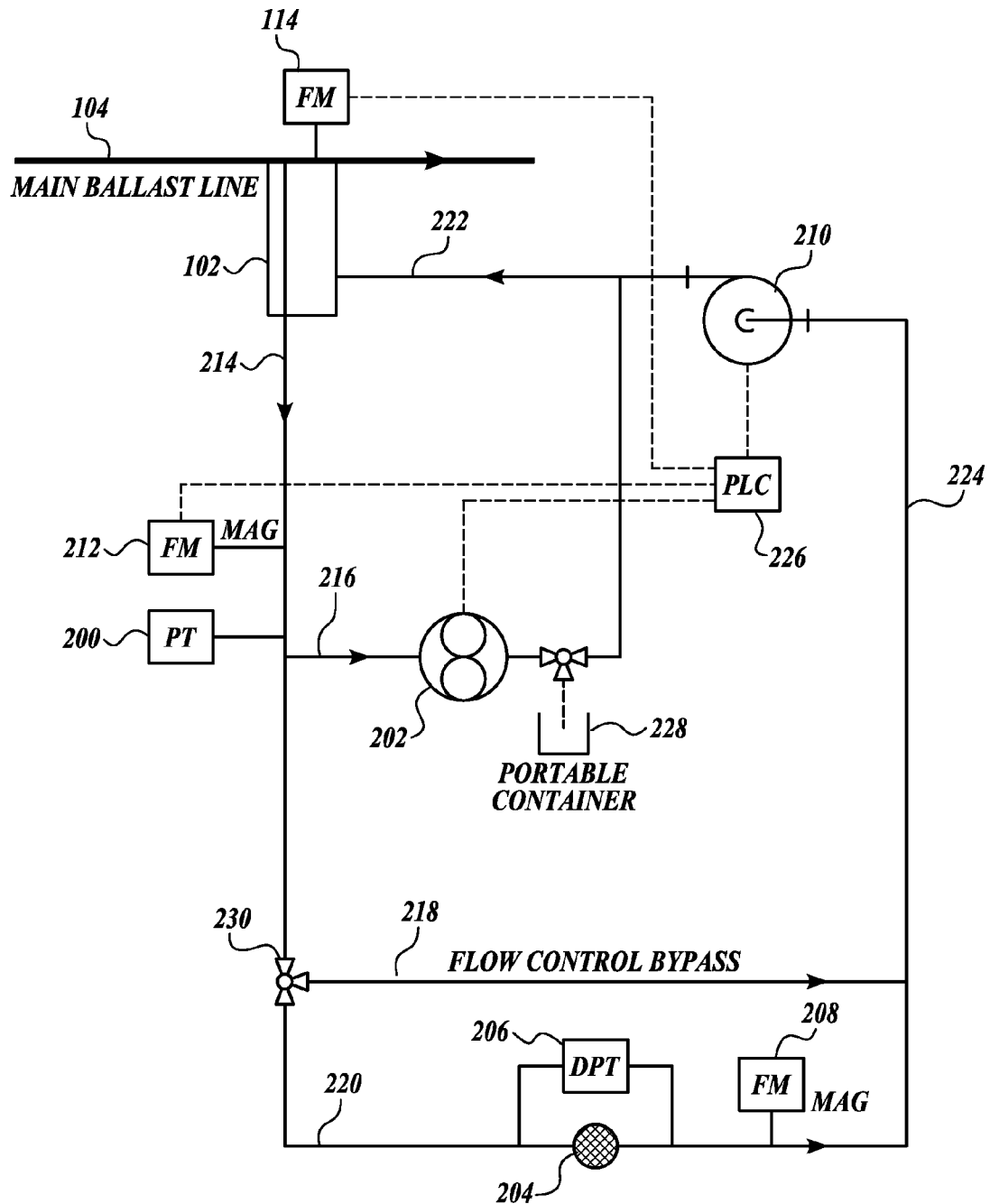
FIG. 8 is a schematic diagram of the ballast water sampling system.

Referring to FIG. 8, a schematic diagram is shown illustrating one embodiment of a sampling system. It is to be appreciated that any piping may include shut-off valves to isolate any instrument and/or drain any section of piping, as well as include the use of temporary piping, such as hoses, connected via quick disconnects.

The system includes the pitot tube assembly 102, which is connected to the ship's ballast water pipe 104. As discussed above, a pitot tube is lowered in the pipe 104 to withdraw sample ballast water at isokinetic conditions. A flow meter is also placed in the pipe 104 to measure the flow velocity of the ship's ballast water flow. The sample ballast water is transferred via line 214. Line 214 is sensed for flow rate (the sample ballast water flow rate), such as via a magnetic flow meter 212. The velocity at the pitot tube 112 can be calculated, for example from flow rate and pipe diameters. The pressure in line 214 may be sensed with the pressure transmitter 200.

The line 214 branches into three branch lines 216, 218, and 220. Branch line 216 leads to a variable speed peristaltic pump 202. Pump 202 is for taking a portion of the sample ballast water to be used for testing. Branch line 216 then connects to the inlet sample return line 222, which allows return of the sample ballast water to the ballast water pipe 104. Branch line 220 includes a filter 204 and a differential pressure transmitter 206 for monitoring the pressure drop in the filter 204. A flow meter, such as a magnetic flow meter 208, can be provided on line 220. The flow through the filter 204 is controlled by the variable speed centrifugal pump 210. Branch line 218 is for receiving the excess flow to maintain isokinetic flow if the filter 204 is disconnected. A flow control valve 230 controls the flow rate through the filter 204. If the filter 204 is not present, all the water passes through the bypass line 218. Branch lines 218 and 220 combine into combined line 224, which leads to the variable speed centrifugal pump 210.

The pump 210 controls the water flow from the pitot tube assembly 102 through the filter 204 and bypass loop 218. The PLC controller 226 may change the speed of the pump 210 to maintain an isokinetic sampling condition at the pitot tube 112. The flow velocity of the ship's ballast water pipe 104 is determined by the flow sensor 114, which can be at the lower end of the pitot wand 110. The flow velocity through the pitot tube may be determined by the flow sensor 212 on the sample water pipe 214. Both flow signals may be transmitted to the PLC controller 226, and the difference in flow velocities can be compared, and, when a difference is sensed, the flow velocity at the pitot tube can be adjusted by the pump 210. Pump 210 can maintain the flow velocity of the sample ballast water through the pitot tube as close as possible to the ship's ballast water flow velocity in pipe 104. While one embodiment of a control system is described, it is to be appreciated that other configurations are possible. For example, a constant flow can be maintained by the pump 210, while a bypass loop with a control valve from the pump discharge to the pump suction controls the amount of flow velocity at the pitot tube.

The circulation pump 210 can be located downstream of the filter 204 and all suctions to subsystems. This means that there is no risk of organism death before being drawn through the filter or into another of the subsystems.

In order to maintain an isokinetic sampling condition at the pitot assembly, most of the sampled water may pass through the filter or a bypass line. If the filter is not in use but other components are operational, the bypass line may be used or an isokinetic condition may not exist at the sample point.

In one embodiment, the circulation pump 210 may pull fluid from the ballast water pipe 104 through the filter 204. A flow meter 208 may measure the flow rate through the filter 204, and the controller PLC 226 may integrate this value to determine the volume of filtered fluid. This measurement can be compared to flow measurements taken from the ballast main pipe 104 to determine the relative scale of the sample fluid to the bulk fluid flow. A ratio of flows can be controlled by the pump 210. In one embodiment, the filter 204 can be a bag-type filter.

The peristaltic pump 202 allows the sample ballast water to pass through the pump without coming into contact with the pump gear, seals, or moving parts. Since the ballast water is gently moving through the pump, the risk of organism mortality is low. The sample is collected in the portable container 228, for example, downstream from the peristaltic pump 202. In one embodiment, the peristaltic pump 202 can rotate quickly, thus pulling a full sample, such as several liters, over a short duration of time. In another embodiment, the peristaltic pump may rotate continuously and slowly, giving a continuous sample over a long period of the ballast water discharging event. In a third embodiment, the peristaltic pump 202 can rotate intermittently, giving discrete samples over the discharge event. These samples could be combined or treated separately. The samples can be put into suitable storage containers, such as 228, for transportation to off-site facilities for analysis.

The sample pitot tube is designed to operate at isokinetic conditions. Most of the current ballast water testing guidance recommends a diameter that is larger than the isokinetic diameter. As discussed previously, this is not desirable in the present embodiment due to space constraints, for example. As disclosed herein, the system uses a pump 210 to be able to modify flow velocities to match the different ballast flow velocities on different vessels, while using the same common sampling pitot tube. This allows a smaller pitot tube to be used with a variety of different vessels.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for taking a sample of ballast water, comprising:
   withdrawing a sample of ballast water via a tube inserted in a ballast water pipe, wherein the tube includes a sample inlet, and isokinetic sampling is achieved via a pump that controls the flow rate of the sample ballast water through the tube inlet by comparing a fluid velocity of the ballast water pipe with a fluid velocity of the sample ballast water through the tube;
   controlling the flow of water through the sample tube inlet when a flow velocity of the ballast water pipe is sensed to be different than a velocity of the ballast water in the pipe;
   withdrawing a portion of the sample ballast water for testing; and
   returning remaining sample ballast water to the ballast water pipe.

2. The method of claim 1, wherein the sample ballast water is withdrawn and returned via a pitot tube assembly comprising a housing and a wand inside the housing, wherein sample ballast water is withdrawn through the wand, and sample ballast water is returned via the housing.

3. The method of claim 2, further comprising extending the wand from within the housing to reach a sampling location inside the ballast water pipe.

4. The method of claim 2, wherein the wand seals against the housing, and sample ballast water is withdrawn from a location above the seal, and sample ballast water is returned below the seal.

5. The method of claim 2, wherein the pitot tube assembly is attached to the ballast water pipe via an isolation valve.

6. The method of claim 1, wherein a second pump is operated to withdraw a portion of the ballast water sample for testing.

\* \* \* \* \*